(12) United States Patent
Waymouth et al.

(10) Patent No.: US 9,944,630 B1
(45) Date of Patent: Apr. 17, 2018

(54) DITHIOLANE CARBONATE MONOMERS AND POLYMERS THEREOF

(71) Applicant: The Board of Trustees of the Leland Stanford Junior University, Stanford, CA (US)

(72) Inventors: Robert M. Waymouth, Stanford, CA (US); Gregg Barcan, Philadelphia, PA (US); Xiangyi Zhang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/417,709

(22) Filed: Jan. 27, 2017

Related U.S. Application Data

(63) Continuation of application No. 14/976,598, filed on Dec. 21, 2015, now Pat. No. 9,556,308.

(60) Provisional application No. 62/095,247, filed on Dec. 22, 2014.

(51) Int. Cl.
| | | |
|---|---|---|
| C07D 409/12 | (2006.01) | |
| C08L 69/00 | (2006.01) | |
| C08J 3/075 | (2006.01) | |
| A61K 49/04 | (2006.01) | |
| A61K 33/24 | (2006.01) | |
| A61K 9/51 | (2006.01) | |
| A61K 9/107 | (2006.01) | |
| A61K 47/34 | (2017.01) | |
| A61K 31/12 | (2006.01) | |
| C08G 64/02 | (2006.01) | |
| C08G 64/18 | (2006.01) | |

(52) U.S. Cl.
CPC .......... *C07D 409/12* (2013.01); *A61K 9/1075* (2013.01); *A61K 9/5146* (2013.01); *A61K 31/12* (2013.01); *A61K 33/24* (2013.01); *A61K 47/34* (2013.01); *A61K 49/04* (2013.01); *C08G 64/025* (2013.01); *C08G 64/183* (2013.01); *C08J 3/075* (2013.01); *C08L 69/00* (2013.01); *C08J 2369/00* (2013.01); *C08L 2203/02* (2013.01)

(58) Field of Classification Search
USPC ........................ 525/418; 424/133.1
See application file for complete search history.

(56) References Cited

U.S. PATENT DOCUMENTS

| 8,617,524 B2 | 12/2013 | Marat |
| 2010/0135942 A1 | 6/2010 | Marat |
| 2010/0197759 A1 | 8/2010 | Marat |

OTHER PUBLICATIONS

Wei, et al., Reduction-Responsive Disassemblable Core-Cross-Linked Micelles Based on Poly(ethylene glycol)-b-poly(N-2-hyclroxypropyl methacrylamide)-Lipoic Acid Conjugates for Triggered Intracellular Anticancer Drug Release, Journal of American Chemical Society, Biomacromolecules, 2012, vol. 13, pp. 2429-2438.

Balakirev, et al., Lipoic acid-derived amphiphiles for redox-controlled DNA delivery, 2000 Elsevier Science Ltd., Chemistry & Biology 2000, vol. 7, pp. 813-819, published Sep. 19, 2000.

Roux, et al., Synthesis, Characterization of Dihydrolipoic Acid Capped Gold Nanoparticles, and Functionalization by the Electroluminescent Luminol, Journal of the American Chemical Society, Langmuir 2005, vol. 21, pp. 2526-2536.

Zhan, et al., Controlling the Architecture, Coordination, and Reactivity of Nanoparticle Coating Utilizing an Amino Acid Central Scaffold, Journal of the American Chemical Society, 2015, vol. 137, pp. 16084-16097.

Tang, et al., Lipoates as building blocks of sulfur-containing branched macromolecules†, The Royal Society of Chemistry 2015, Polym. Chem., 2015, vol. 6, pp. 6936-6945.

Gyarmati, et al., Reversible disulphide formation in polymer networks: A versatile functional group from synthesis to applications, European Polymer Journal, Elsevier Ltd., Aug. 7, 2012, vol. 49, pp. 1268-1286.

Bang, et al., Poly(disulfide)s, Chemical Science, 2012, vol. 3, p. 1752.

Black, et al., Disulfide exchange: exposing supramolecular reactivity through dynamic covalent chemistry, Chem. Soc. Rev., 2014, vol. 43, p. 1861.

(Continued)

*Primary Examiner* — Terressa Boykin
(74) *Attorney, Agent, or Firm* — Heslin Rothenberg Farley & Mesiti, P.C.; Philip Hansen

(57) ABSTRACT

1,2-Diothiolane monomers are disclosed, as are polymers and hydrogels comprising the polymers. Processes for preparing the monomers, polymers and compositions are also disclosed. The monomers have the formula:

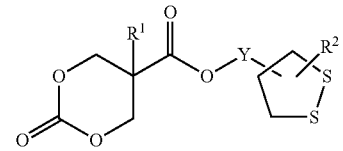

The polymers may include the following repeating units:

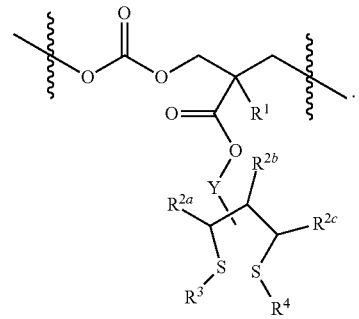

16 Claims, No Drawings

(56) References Cited

OTHER PUBLICATIONS

Bang, et al., Cell-penetrating poly(disulfide)s: focus on substrate-initiated co-polymerization†, The Royal Society of Chemistry, Polym. Chem., 2014, vol. 5, p. 2433.

Sadownik, et al., Polymerized Liposomes Formed under Extremely Mild Conditions, American Chemical Society, J. Am. Chem. Soc., 1986, vol. 108, pp. 7789-7791.

Kisanuki, et al., Ring-Opening Polymerization of Lipoic Acid and Characterization of the Polymer, Wiley Periodicals, Inc., Journal of Polymer Science: Part A: Polymer Chemistry, (2010) vol. 48, 5247-5253.

Sakai, et al., Self-Organizing Surface-Initiated Polymerization: Facile Access to Complex Functional Systems, Journal of the American Chemical Society, 2011, vol. 133, pp. 15224-15227.

Bang, et al., Substrate-Initiated Synthesis of Cell-Penetrating Poly(disulfide)s Journal of the American Chemical Society, Jan. 30, 2013, vol. 135, pp. 2088-2091.

Li, et al., Reversibly Stabilized Multifunctional Dextran Nanoparticles Efficiently Deliver Doxorubicin into the Nuclei of Cancer Cells, Wiley InterScience, Angew. Chem. Int. Ed. 2009, vol. 48, pp. 9914-9918.

Rosenthal, et al., Green Polymer Chemistry: Living Dithiol Polymerization via Cyclic Intermediates, American Chemical Society, Biomacromolecules, 2012, vol. 13, pp. 154-164.

Yu, et al., Disulfide Cross-Linked Polyurethane Micelles as a Reduction-Triggered Drug Delivery System for Cancer Therapy, Adv. Healthcare Mater. 2014, 3, 752-760.

Pratt, et al., Tagging alcohols with cyclic carbonate: a versatile equivalent of (meth)acrylate for ring-opening polymerization, The Royal Society of Chemistry 2008, Chem. Commun., 2008, pp. 114-116.

Kloxin, C.J., Bowan, Covalent adaptable networks; C.N. Chem. Soc. Rev. 2013, 42, 7161-7173.

Li, et al., Self-Healing Supramolecular Self-Assembled Hydrogels Based on Poly (L-glutamic acid), Biomacromolecules, 2015, 16 (11), pp. 3508-3518.

Datta, et al., Controlled Organocatalytic Ring-Opening Polymerization of $\epsilon$-Thionacaprolactone; Macromolecules 2016, 49, 774-780.

DITHIOLANE CARBONATE MONOMERS AND POLYMERS THEREOF

CROSS REFERENCE TO RELATED APPLICATIONS

This application is a continuation of U.S. patent application Ser. No. 14/976,598, filed Dec. 21, 2015, now allowed, which claims priority from U.S. Provisional Application 62/095,247, filed Dec. 22, 2014. The entire contents of these applications are incorporated herein by reference.

GOVERNMENT RIGHTS STATEMENT

This invention was made with Government support under grant CHE-1306730 awarded by the National Science Foundation. The Government has certain rights in the invention.

FIELD OF THE INVENTION

The present invention generally relates to 1,2-diothiolane monomers, polymers produced from those monomers, and compositions such as hydrogels and micelles comprising the same, and processes for preparing the monomers, polymers and compositions.

BACKGROUND OF THE INVENTION

The formation of disulfide bonds is an attractive strategy for binding together and stabilizing macromolecular structures. This is in part due to the ease in which disulfide bonds can be formed: by the heating of compounds with elemental sulfur, through the oxidation of free thiols (often by only ambient oxygen), or through the ring-opening of a cyclic disulfide. The sulfur-sulfur bonds formed through these methods are reasonably stable for further processing and chemical transformations, but they can be selectively cleaved by light or heat, allowing for network rearrangement, and this has been exploited in the preparation of self-healing materials. Perhaps the most broadly applied condition for the degradation of disulfide bonds is the use of reducing conditions, which has been utilized for intracellular drug delivery by relying on the relatively high concentration of glutathione within cells.

A need exists for new and improved compositions and methods relating to the formation of disulfide bonds in, e.g., macromolecular architectures.

SUMMARY OF THE INVENTION

Briefly, the present invention satisfies the need for new and improved compositions and methods relating to the formation of disulfide bonds in various molecular architectures, including such formation via ring-opening of cyclic disulfides.

In one aspect, the invention provides a compound of the formula (I):

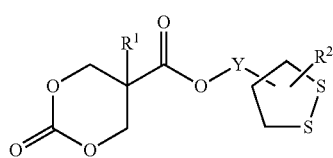

wherein

Y is a linker selected from aliphatic $C_1$-$C_8$ hydrocarbyl in which one or two carbon atoms may optionally be replaced by one or more of —O— and —C(=O)—;

$R^1$ is selected from hydrogen and $C_1$-$C_3$ alkyl; and $R^2$ is selected from hydrogen and $C_1$-$C_3$ alkyl.

In a second aspect, the invention provides a polymer comprising a structural unit of the formula (II):

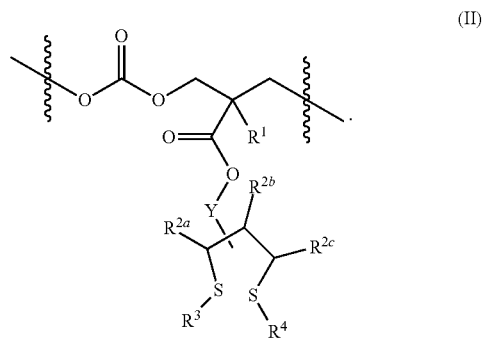

wherein

Y is a linker selected from aliphatic $C_1$-$C_8$ hydrocarbyl in which one or two carbon atoms may optionally be replaced by one or more of —O— and —C(=O)—, and wherein Y is attached to the carbon attached to $R^{2a}$, to the carbon attached to $R^{2b}$, or to the carbon attached to $R^{2c}$;

$R^1$ is selected from hydrogen and $C_1$-$C_3$ alkyl;

$R^{2a}$, $R^{2b}$, and $R^{2c}$, are individually selected from hydrogen and $C_1$-$C_3$ alkyl;

$R^3$ and $R^4$ are hydrogen, or $R^3$ and $R^4$, taken together, form a direct bond between the sulfur atoms to which they are attached, thereby forming a dithiolane ring; or one of $R^3$ and $R^4$ is selected from hydrogen, pyrrolidine-2,5-dione, and propionamide, and the other is a residue of formula (IIIA):

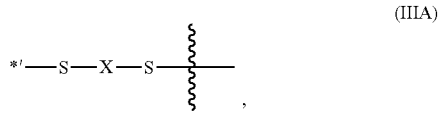

wherein

*' represents the point of attachment to $R^3$ or $R^4$;

X is chosen from $C_1$-$C_{10}$ hydrocarbyl, $C_1$-$C_{10}$ hydrocarbyl substituted with —OH, —$(CH_2)_q$—O—$(CH_2)_r$— and —$(CH_2)_q$[—O—$(CH_2)_r$]$_t$—;

q is 2, or 3;

r is 2, or 3; and t is an integer from 2 to 1000.

In a third aspect, the invention provides a composition comprising the inventive compound. For example, in some embodiments, the invention provides a hydrogel comprising water and a compound containing a structural unit of the formula (II).

In a fourth aspect, the invention provides a process for preparing a compound comprising a structural unit of the formula (II), said process comprising:

performing organocatalytic ring opening polymerization on a compound of formula (I):

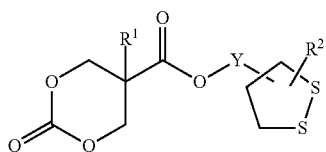

(I)

wherein
Y is a linker selected from a direct bond and aliphatic $C_1$-$C_8$ hydrocarbyl in which one or two carbon atoms may optionally be replaced by one or more of —O— and —C(=O)—;
$R^1$ is selected from hydrogen and $C_1$-$C_3$ alkyl; and
$R^2$ is selected from hydrogen and $C_1$-$C_3$ alkyl,
in the presence of an alcohol, a Lewis base, and a Lewis acid, thereby forming a compound comprising a structural unit of the formula (II):

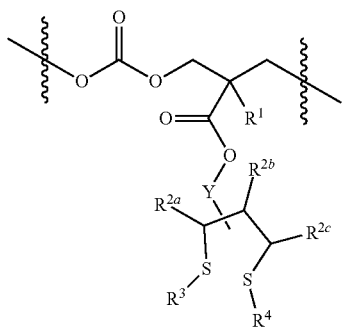

In other aspects, the invention relates to hydrogels, nanoparticles and micelles in which the compounds above are incorporated.

DETAILED DESCRIPTION OF THE INVENTION

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

The term "hydrocarbyl" is a generic term encompassing $C_1$-$C_{10}$ aliphatic, alicyclic and aromatic groups having an all-carbon backbone, except where otherwise stated. Examples of hydrocarbyl groups include alkyl, carbocyclic (e.g., cycloalkyl), alkenyl, cycloalkenyl, alkynyl, aryl, cycloalkylalkyl, cycloalkenylalkyl, and carbocyclic aralkyl, aralkenyl and aralkynyl groups. Within the sub-set of hydrocarbyl groups are those having 1 to 8 carbon atoms, examples including $C_{1-6}$ hydrocarbyl groups, such as $C_{1-4}$ hydrocarbyl groups (e.g., $C_{1-3}$ hydrocarbyl groups or $C_{1-2}$ hydrocarbyl groups). Specific examples of hydrocarbyl groups include any individual value or combination of values selected from $C_1$, $C_2$, $C_3$, $C_4$, $C_5$, $C_6$, $C_7$, $C_8$, $C_9$, and $C_{10}$, hydrocarbyl groups. Hydrocarbyl includes any substituent comprised of hydrogen and carbon as the only elemental constituents.

The term "alkyl" covers both straight chain and branched hydrocarbon structures and combinations thereof. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups are those having 1 to 8 carbon atoms, for example 1-2, 1-3, 1-4, 1-5, 1-6, 1-7, and 1-8 carbon atoms.

Examples of cycloalkyl groups are cyclopropane, cyclobutane, cyclopentane, cyclohexane and cycloheptane. Within the sub-set of cycloalkyl groups are cycloalkyl groups having from 3 to 8 carbon atoms, particular examples being $C_{3-6}$ cycloalkyl groups. Cycloalkyl, if not otherwise limited, refers to monocycles, bicycles and polycycles.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups are those having 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups are those having from 3 to 8 carbon atoms, for example, $C_{3-6}$ cycloalkenyl groups.

Examples of alkynyl groups include, but are not limited to, ethynyl and 2-propynyl (propargyl) groups. Within the sub-set of alkynyl groups are those having 2 to 8 carbon atoms, particular examples being $C_{2-6}$ alkynyl groups, such as $C_{2-4}$ alkynyl groups.

Examples of aryl groups, which are defined below, include substituted and unsubstituted phenyl and naphthyl groups.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, or 5 or 6 ring members. Examples of bicyclic groups are those containing 8, 9, 10, 11 and 12 ring members, and more usually 9 or 10 ring members. Where one or more carbon atoms in a carbocyclic ring system is replaced with a heteroatom, the ring becomes a heterocyclic ring.

Unless otherwise specified, "aryl" and "heteroaryl" mean (i) a phenyl group (or benzene) or a monocyclic 5- or 6-membered heteroaromatic ring containing 1-4 heteroatoms independently selected from O, N, and S; (ii) a bicyclic 9- or 10-membered aromatic or heteroaromatic ring system containing 0-4 heteroatoms independently selected from O, N, and S; or (iii) a tricyclic 13- or 14-membered aromatic or heteroaromatic ring system containing 0-5 heteroatoms independently selected from O, N, and S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl refers to a substituent in which an aryl residue is attached to the parent structure through an alkyl group. Examples are benzyl, phenethyl and the like. Heteroarylalkyl refers to a substituent in which a heteroaryl residue is attached to the parent structure through alkyl.

Heterocycle means a cycloalkyl residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring (e.g., a dithiolane); it may contain additional sulphurs, as well as other heteroatoms. Oxygen heteroaryl is a subset of oxygen heterocycle; examples include furan and oxazole. Sulphur heteroaryl is a subset of sulphur heterocycle; examples include thiophene and thiazine. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Nitrogen heteroaryl is a subset of nitrogen heterocycle; examples include pyridine, pyrrole and thiazole.

The term "halogen" means fluorine, chlorine, bromine or iodine. In one embodiment, halogen may be fluorine or chlorine.

Substituents (e.g. R″) are generally defined when introduced and retain that definition throughout the specification and in all independent claims.

Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention.

In one aspect, the invention provides a compound of the formula (I):

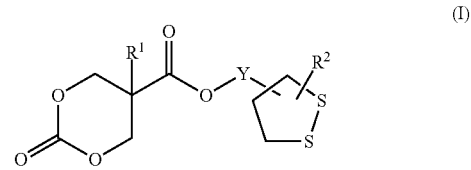

wherein

Y is a linker selected from aliphatic $C_1$-$C_8$ hydrocarbyl in which one or two carbon atoms may optionally be replaced by one or more of —O— and —C(=O)—;

$R^1$ is selected from hydrogen and $C_1$-$C_3$ alkyl; and $R^2$ is selected from hydrogen and $C_1$-$C_3$ alkyl.

Throughout this specification, where it is indicated that "one or two carbon atoms may optionally be replaced by one or more of . . . " it is intended, and a person having ordinary skill in the art will appreciate, that the carbon atom as well as any hydrogen atom(s) attached thereto, are optionally replaced by the recited radicals.

In some embodiments, Y is selected from aliphatic $C_1$-$C_8$ hydrocarbyl, preferably $C_1$-$C_8$ alkyl or alkylcycloalkyl, in which one or two carbon atoms may optionally be replaced by one or more of —O— and —C(=O)—. In some embodiments, Y is —$(CH_2)_n$—$(O)_m$—$(C=O)_p$—*, wherein * represents the point of attachment to the dithiolane ring; n is 1, 2, 3, or 4; m is 0 or 1; and p is 0 or 1. For example, in some embodiments, Y is —$(CH_2)_n$—O—C(=O)—*. In particular embodiments, n is 2. In some particular embodiments, $R^1$ and/or $R^2$ is methyl. In some embodiments, both $R^1$ and $R^2$ are methyl. In some embodiments Y is —$(CH_2)_u$—O—C(=O)—$(CH_2)_v$—*, wherein u is 2, 3, or 4; and v is an integer from 1 to 6.

In some embodiments, the compound of formula (I) is a compound having the formula (IA):

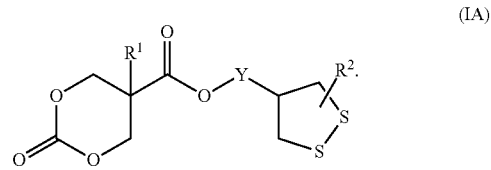

For example, in some embodiments, the compound is of the formula (IA-i):

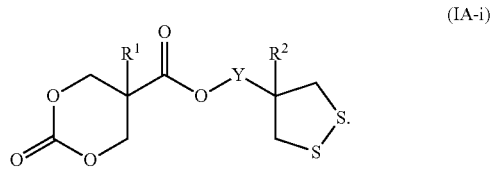

In some embodiments, the compound of formula (I) is a compound having the formula (IB):

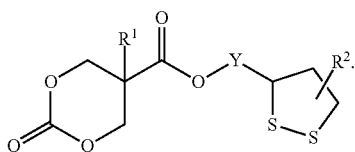

(IB)

For example, in some embodiments, the compound is of the formula (IB-i):

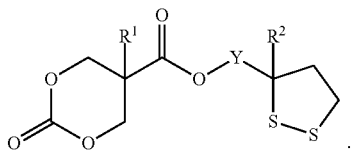

(IB-i)

In a second aspect, the invention provides a polymer comprising a structural unit of the formula (II):

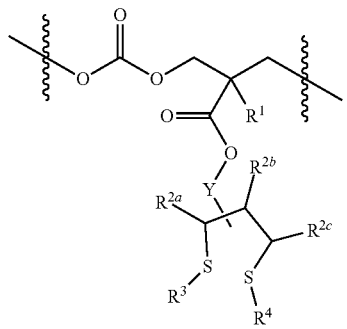

(II)

wherein
Y is a linker selected from aliphatic $C_1$-$C_8$ hydrocarbyl in which one or two carbon atoms may optionally be replaced by one or more of —O— and —C(=O)—, and wherein Y is attached to the carbon attached to $R^{2a}$, to the carbon attached to $R^{2b}$, or to the carbon attached to $R^{2c}$;
$R^1$ is selected from hydrogen and $C_1$-$C_3$ alkyl;
$R^{2a}$, $R^{2b}$, and $R^{2c}$, are individually selected from hydrogen and $C_1$-$C_3$ alkyl;
$R^3$ and $R^4$ are hydrogen, or $R^3$ and $R^4$, taken together, form a direct bond between the sulfur atoms to which they are attached, thereby forming a dithiolane ring; or one of $R^3$ and $R^4$ is selected from hydrogen, pyrrolidine-2,5-dione, and propionamide, and the other is a residue of formula (IIIA):

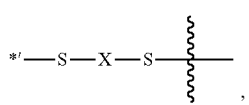

(IIIA)

wherein
*' represents the point of attachment to $R^3$ or $R^4$;
X is chosen from $C_1$-$C_{10}$ hydrocarbyl, $C_1$-$C_{10}$ hydrocarbyl substituted with —OH, —$(CH_2)_q$—O—$(CH_2)_r$— and —$(CH_2)_q[$—O—$(CH_2)_r]_t$—;
q is 2, or 3;
r is 2, or 3; and
t is an integer from 2 to 1000.

In some embodiments, Y is selected from aliphatic $C_1$-$C_8$ hydrocarbyl in which one or two carbon atoms may optionally be replaced by one or more of —O— and —C(=O)—.

In some embodiments, Y is —$(CH_2)_n$—$(O)_m$—$(C=O)_p$—*, wherein * represents the point of attachment to the carbon attached to $R^{2a}$, the carbon attached to $R^{2b}$, or the carbon attached to $R^{2c}$; n is, 1, 2, 3, or 4; m is 0 or 1; and p is 0 or 1. For example, in particular embodiments, Y is —$(CH_2)_n$—O—C(=O)—*. In more particular embodiments, n is 2. In some embodiments, $R^1$ and/or $R^{2b}$ are methyl. In particular embodiments both $R^1$ and $R^{2b}$ are methyl, $R^{2a}$ and $R^{2c}$ are hydrogen, and Y is —$(CH_2)_n$—O—C(=O)—* wherein n is 2 and * represents the point of attachment to the carbon attached to $R^{2b}$. In some embodiments Y is —$(CH_2)_u$—O—C(=O)—$(CH_2)_v$—*, wherein u is 2, 3, or 4; and v is an integer from 1 to 6. In particular embodiments, $R^1$ is methyl, $R^{2a}$, $R^{2b}$ and $R^{2c}$ are hydrogen, and Y is —$(CH_2)_u$—O—C(=O)—$(CH_2)_v$—*, wherein u is 2 and v is 2, 3, or 4, preferably 4.

In some embodiments, the inventive polymer comprises a structural unit of the formula (IIA):

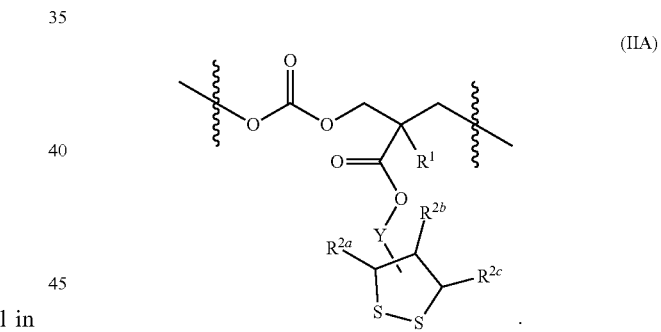

(IIA)

In some embodiments, the inventive polymer comprises a structural unit of the formula (IIB) or (IIC):

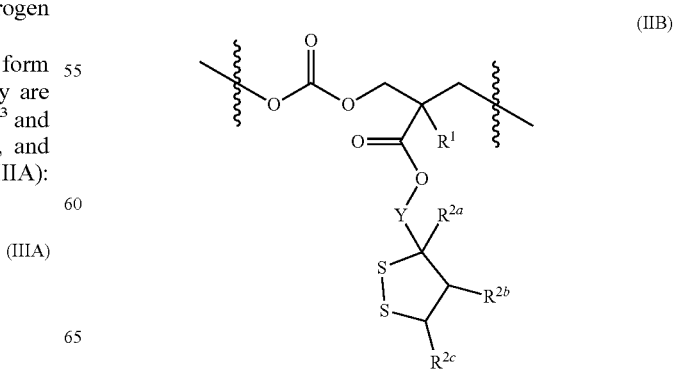

(IIB)

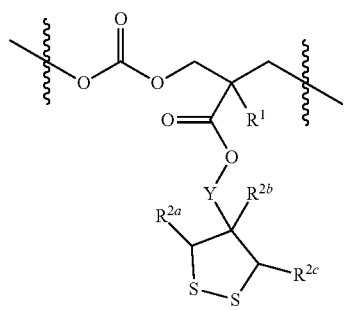
(IIC)

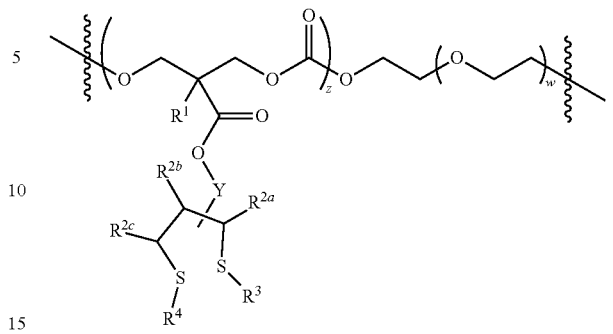
(IIE)

wherein z is 1-25 or a triblock polymer of formula IIf:

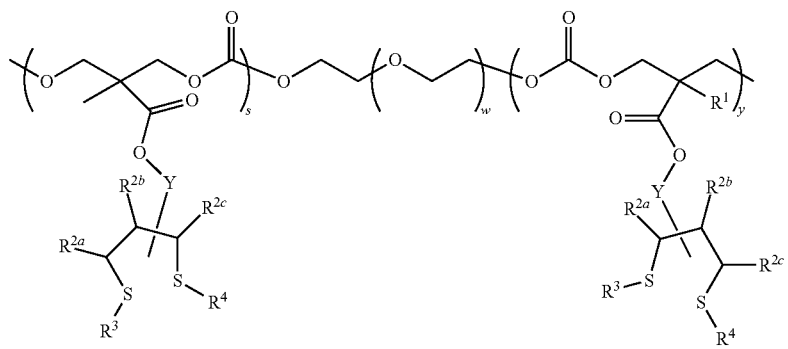

wherein s and y are 2 to 10. In some embodiments w is 300-350; in some embodiments w is 80-120; in some embodiments w is 400-500; in some embodiments w is 750-850. It will be understood that each side-chain of formula In some embodiments, the inventive polymer comprises a structural unit of the formula (IID):

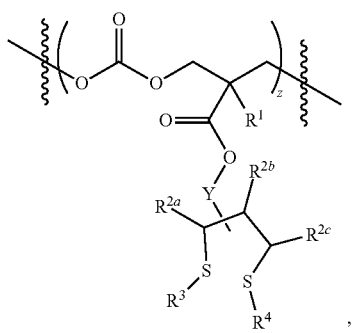
(IID)

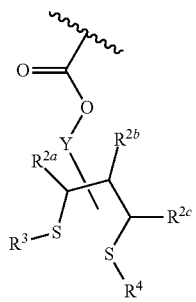

wherein z is 1-25, preferably 2-10.

In some embodiments, the inventive polymer additionally comprises a structural unit of the formula (IV):

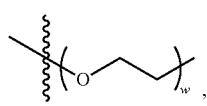
(IV)

wherein
w is 1-1000.

For example, in some embodiments, the invention provides a polymer having the formula (IIE):

need not be identical as long as all fall within the definitions of Y and of the R-groups. This will become clearer from the examples below in which the side-chains are different.

In a third aspect, the invention provides a composition comprising the polymers described above. For example, in some embodiments, the invention provides a hydrogel comprising water and a compound containing a structural unit of the formula (II) wherein one of $R^3$ and $R^4$ is selected from hydrogen, pyrrolidine-2,5-dione, and propionamide, and the other is a residue of formula (IIIA):

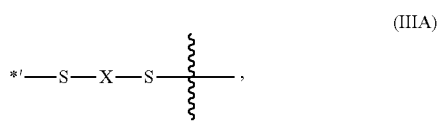 (IIIA)

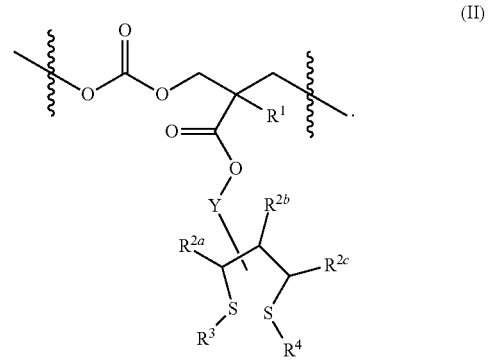 (II)

In a fourth aspect, the invention provides a process for preparing a polymer containing a structural unit of the formula (II). The process comprises:

performing organocatalytic ring opening polymerization on a compound of formula (I):

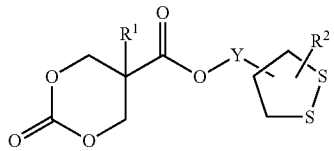

in the presence of an alcohol, a Lewis base, and a Lewis acid, thereby forming a polymer or oligomer comprising a structural unit of the formula (II):

In some embodiments, the alcohol is TMS-propanol. In some embodiments the alcohol is polyethylene glycol (PEG).

In some embodiments, the Lewis base (which serves as an organic catalyst) is diazabicyclo [5.4.0] undec-7-ene (DBU).

In some embodiments, the Lewis acid is a thiourea (TU).

EXAMPLES

Two trimethylene carbonate/dithiolane monomers were chosen as the basis for a number of exemplary polymers. The first trimethylene carbonate/dithiolane monomer was based on methyl asparagusic acid and was nicknamed TMCDT. The synthesis of TMCDT was carried out in 2 steps from the known carboxylic acids (Scheme 1).

Scheme 1. Synthesis of TMCDT monomer and ABA triblock copolymers

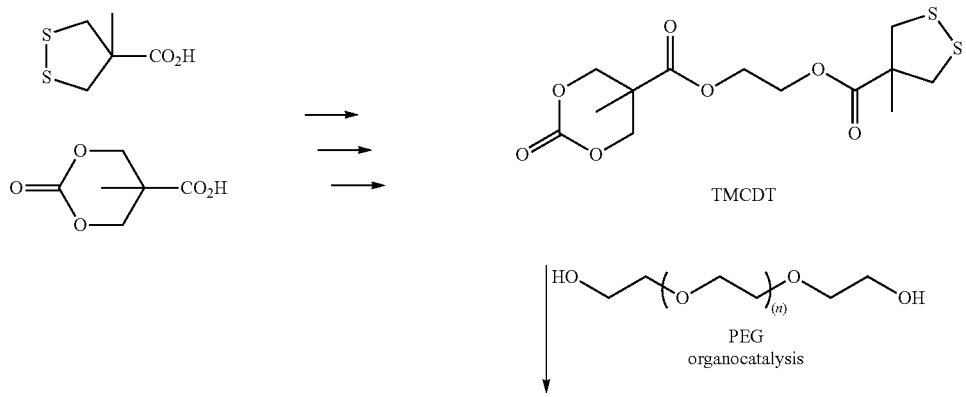

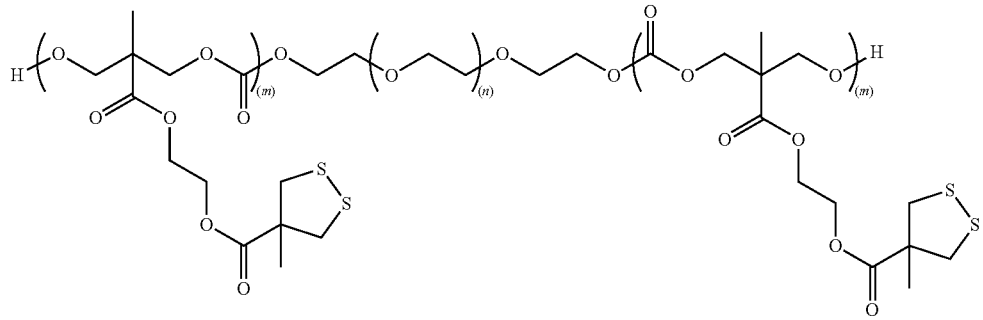

Triblock copolymers of p(TMCDT-PEG-TMCDT), containing short TMCDT sequences (DP ~5) were generated by the ring-opening of TMCDT employing 5 mol % 1,8-diazabicyclo [5.4.0]undec-7-ene (DBU) and 1-[3,5-bis(trifluoromethyl)phenyl]-3-cyclohexylthiourea (TU) in $CH_2Cl_2$ from telechelic PEG diols ($M_n$=4.6, 14, 20, and 35 kDa). Overlays of the GPC refractive index and UV traces demonstrated efficient initiation from PEG and close inspection of the $^1H$ NMR spectra showed the dithiolane ring to be intact with no sign of ring opening under the reaction conditions. Triblock synthesis was performed as follows.

Synthesis of TMCDT

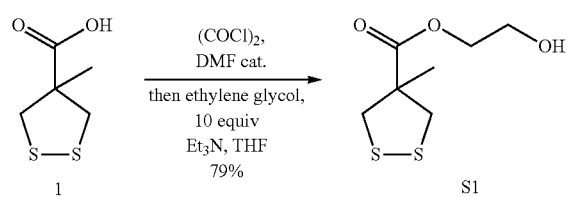

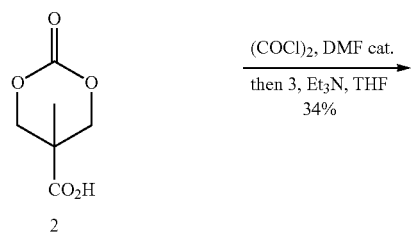

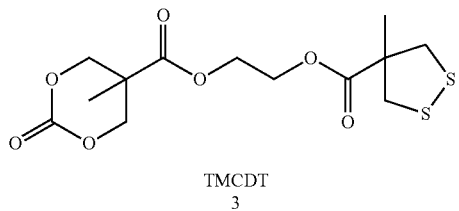

Experimental Procedures

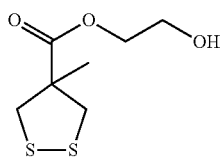

In a dry 1 L flask fitted with a magnetic stir bar, 4-methyl-1,2-dithiolane-4-carboxylic acid 1 (10.7 g, 65.1 mmol) was dissolved in THF (430 mL), the solution was then placed under $N_2$ and DMF (1.0 mL) was added. $(COCl)_2$ (9.1 g, 71.6 mmol, 1.1 equiv) was added dropwise at ambient temperature and the reaction was aged for 3.5 hours. Ethylene glycol (40.4 g, 651 mmol, 10 equiv) was combined with THF (200 mL) in a 1 L flask fitted with a stirbar. $Et_3N$ (28.2 mL, 195 mmol, 3 equiv) was added to the ethylene glycol solution, followed by DMAP (153 mg, 1.63 mmol, 0.025 equiv) and the mixture was cooled in an ice bath under $N_2$. The acid chloride solution was then added via cannula to the ethylene glycol/$Et_3N$ solution over 1 h. Following addition, the reaction was brought to ambient temperature and allowed to stir overnight (14 h). The reaction was then vacuum filtered through fritted funnel packed with celite and the ammonium chloride cake was washed with THF until no product could be detected from the eluent by TLC (1:1 EtOAc:hexanes). The solvent was removed via rotary evaporation and the residue was chromatographed on silica gel using 30% EtOAc in hexanes. Removal of solvent provided the product S1 as a yellow oil (10.7 g, 79% yield). IR (neat) 2934, 2874, 1725, 1453, 1414, 1376, 1291, 1223, 1171, 1071, 1018, 887, 844 $cm^{-1}$; $^1H$ NMR ($CDCl_3$) δ 1.53 (s, 3H), 2.97 (d, 2H, J=11.6 Hz), 3.71 (d, 2H, J=11.6 Hz), 3.83-3.87 (m, 2H), 4.29-4.33 (m, 2H); $^{13}C$ NMR ($CDCl_3$) δ 24.0, 47.9, 58.2, 61.3, 67.3, 174.9; MS (GCMS) calc 208.0, found 208.0.

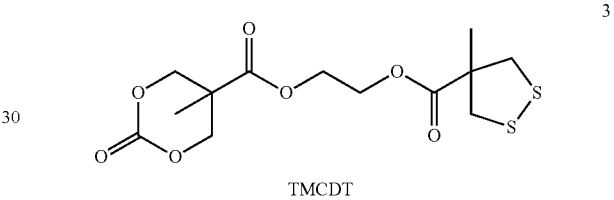

In a 500 mL flask, 5-methyl-2-oxo-1,3-dioxane-5-carboxylic acid 2 (7.0 g, 44 mmol) was dissolved in THF (225 mL) and placed under $N_2$. DMF (170 μL) was added, followed by the dropwise addition of $(COCl)_2$ (3.7 mL, 46 mmol, 1.05 equiv) and the reaction was aged for 2 hours. S1 (10 g, 48 mmol, 1.1 equiv) was charged in a 1 L flask and THF (200 mL) was added, followed by $Et_3N$ (21.0 mL, 144 mmol, 3 equiv) and DMAP (586 mg, 4.80 mmol, 0.1 equiv). The acid chloride solution was charged into an addition funnel and added dropwise into the solution of S1 under $N_2$ over a period of 2 hours. The reaction was allowed to stir overnight (15 h), after which time the reaction was vacuum filtered through a fritted funnel packed with celite and the filter cake was washed with THF until no more product could be detected from the eluent by TLC (1:1 EtOAc:hexanes). The solvent was removed via rotary evaporation and the residue was chromatographed on silica gel (30% EtOAc in hexanes) to give the crude product (11.3 g) after evaporation of the solvent. The heavy yellow oil was then dissolved in dichloromethane and treated with activated carbon, after which, it was recrystallized from dichloromethane/diethyl ether to give the product as a light yellow solid (5.2 g, 34% yield) m.p.: 51-54° C.; IR (neat) 2978, 2964, 2939, 2883, 1752, 1723, 1464, 1407, 1333, 1287, 1236, 1221, 1173, 1127, 1094, 1043 $cm^{-1}$; $^1H$ NMR ($CDCl_3$) δ 1.33 (s, 3H), 1.49 (s, 3H), 2.94 (d, J=11.6 Hz, 2H), 3.67 (d, J=11.6 Hz, 2H), 4.17-4.23 (m, 2H), 4.38-4.47 (m, 4H), 4.67-4.72 (m, 2H); $^{13}C$ NMR ($CDCl_3$) δ 17.5, 23.8, 40.3, 47.6, 57.8, 62.7, 63.8, 72.9, 147.2, 170.9, 174.1; MS (ESI) M+H calc. 351.1, found 351.4.

Preparation of Triblock Copolymers

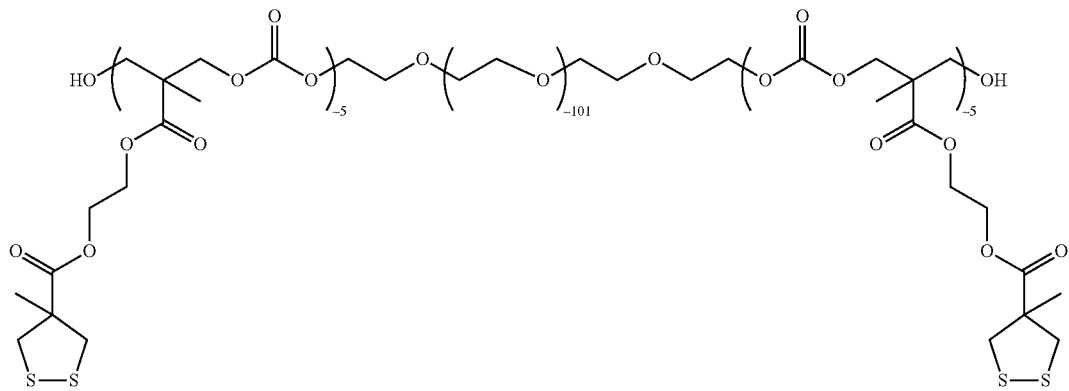

Copolymer 1
PEG4.6K/TMCDT DP 10

In a glove box under $N_2$, thiourea (10.6 mg, 28.7 μmol), monomer (196 mg, 559 μmol), and PEG 14K (200 mg) were added to a 4 mL vial fitted with a stir bar and were subsequently dissolved in dichloromethane (1.3 g). DBU (4.2 μL, 28 μmol) was added to initiate polymerization and the vial was sealed with a screw cap. After 6 hours, the reaction was quenched by the addition of excess benzoic acid and precipitated twice into diethyl ether (2×400 mL) to give PEG4.6K/TMCDT DP10 as a light yellow solid. $M_n$=~8,100 g/mol ($^1$H NMR), PDgI=1.16 (GPC); $^1$H NMR (CDCl$_3$) δ 1.18-1.30 (m, 3H), 1.48 (br s, 3H), 2.93 (d, J=11.7 Hz, 2H), 3.41-3.84 (m, ~41H), 4.21-4.46 (m, ~8.5H).

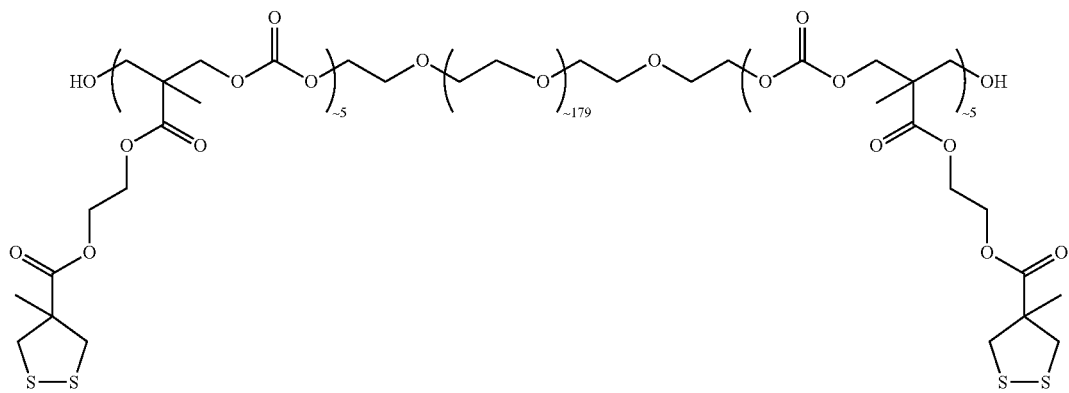

Copolymer 2
PEG8K/TMCDT DP 10

In a glove box under $N_2$, thiourea (10.6 mg, 28.7 μmol), monomer (200 mg, 570 μmol), and PEG 8K (380 mg) were added to a 4 mL vial fitted with a stir bar and were subsequently dissolved in dichloromethane (1.3 g). DBU (4.2 μL, 28 μmol) was added to initiate polymerization and the vial was sealed with a screw cap. After 4 hours, the reaction was quenched by the addition of excess benzoic acid and precipitated twice into diethyl ether (2×400 mL) to give PEG8K/TMCDT DP10 as a light yellow solid (420 mg, 72% yield). $M_n$=~11,500 g/mol NMR), PDI=1.15 (GPC); $^1$H NMR (CDCl$_3$) δ 1.18-1.30 (m, 3H), 1.48 (br s, 3H), 2.93 (d, J=11.7 Hz, 2H), 3.41-3.84 (m, ~72H), 4.21-4.46 (m, ~8H).

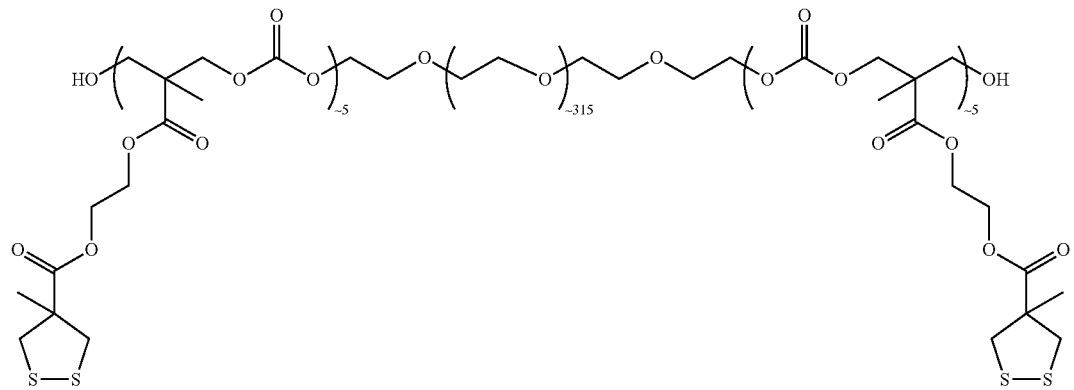

Copolymer 3
PEG14K/TMCDT DP 10

In a glove box under $N_2$, thiourea (15.6 mg, 42.2 μmol), monomer (300 mg, 856 μmol), and PEG 14K (1.0 g) were added to a 20 mL vial fitted with a stir bar and were subsequently dissolved in dichloromethane (2.0 g). DBU (6.4 μL, 43 μmol) was added to initiate polymerization and the vial was sealed with a screw cap. After 3 hours, the reaction was quenched by the addition of excess benzoic acid and precipitated twice into diethyl ether (2×800 mL) to give PEG14K/TMCDT DP10 as a light yellow solid (910 mg, 70% yield). $M_n$=~17,500 g/mol NMR), PDI=1.15 (GPC); $^1$H NMR (CDCl$_3$) δ 1.20-1.30 (m, 3H), 1.49 (s, 3H), 2.94 (d, J=11.6 Hz, 2H), 3.61-3.74 (m, ~131H), 4.25-4.45 (m, 8.3H).

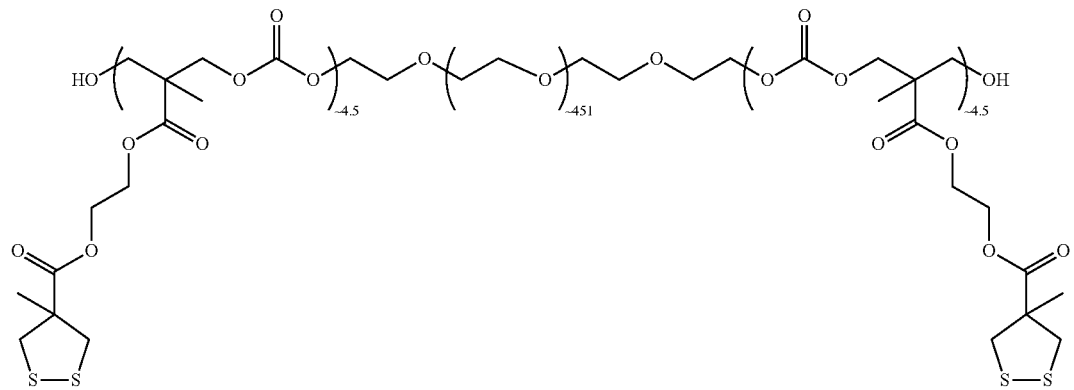

Copolymer 4
PEG20K/TMCDT DP 9

In a glove box under $N_2$, thiourea (5.6 mg, 15 μmol), monomer (105 mg, 300 μmol), and PEG 20K (500 mg) were added to a 20 mL vial fitted with a stir bar and were subsequently dissolved in dichloromethane (1.1 g). DBU (2.2 μL, 15 μmol) was added to initiate polymerization and the vial was sealed with a screw cap. After 8 hours, the reaction was quenched by the addition of excess benzoic acid and precipitated twice into diethyl ether (2×500 mL) to give PEG20K/TMCDT DP9 as a light yellow solid (448 mg, 74% yield). $M_n$=~23,200 g/mol NMR), PDI=1.35 (GPC); $^1$H NMR (CDCl$_3$) δ 1.18-1.30 (m, 3H), 1.48 (s, 3H), 2.93 (d, J=11.6 Hz, 2H), 3.55-3.75 (m, ~206H), 4.25-4.45 (m, 8.3H).

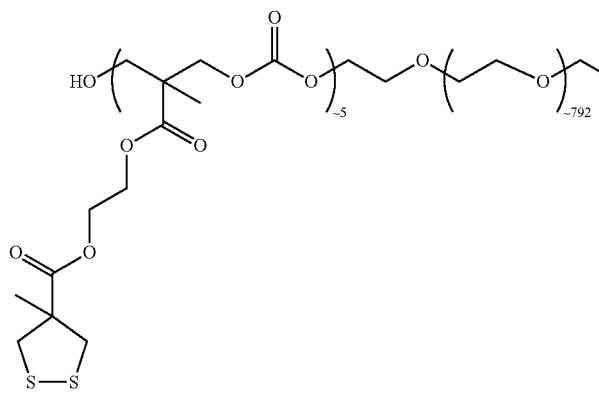
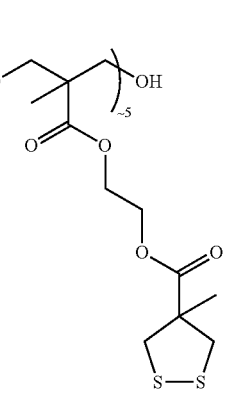

Copolymer 5
PEG35K/TMCDT DP 10

In a glove box under N₂, thiourea (6.3 mg, 17 μmol), monomer (120 mg, 343 μmol), and PEG 35K (682 mg) were added to a 20 mL vial fitted with a stir bar and were subsequently dissolved in dichloromethane (2.8 g). DBU (2.2 μL, 17 μmol) was added to initiate polymerization and the vial was sealed with a screw cap. After 7.5 hours, the reaction was quenched by the addition of excess benzoic acid and precipitated twice into diethyl ether (2×500 mL) to give PEG35K/TMCDT DP10 as a light yellow solid (505 mg, 63% yield). $M_n$=38,500 g/mol (¹H NMR), PDI=1.17 (GPC); ¹H NMR (CDCl₃) δ 1.20-1.30 (m, 3H), 1.49 (s, 3H), 2.94 (d, J=11.6 Hz, 2H), 3.51-3.77 (m, ~310H), 4.23-4.42 (m, 8.3H).

The second trimethylene carbonate/dithiolane monomer was based on lipoic acid, 5-(1,2-dithiolan-3-yl)pentanoic acid, and was nicknamed TMCLA. The synthesis of TMCLA was carried out in similar fashion to TMCDT.

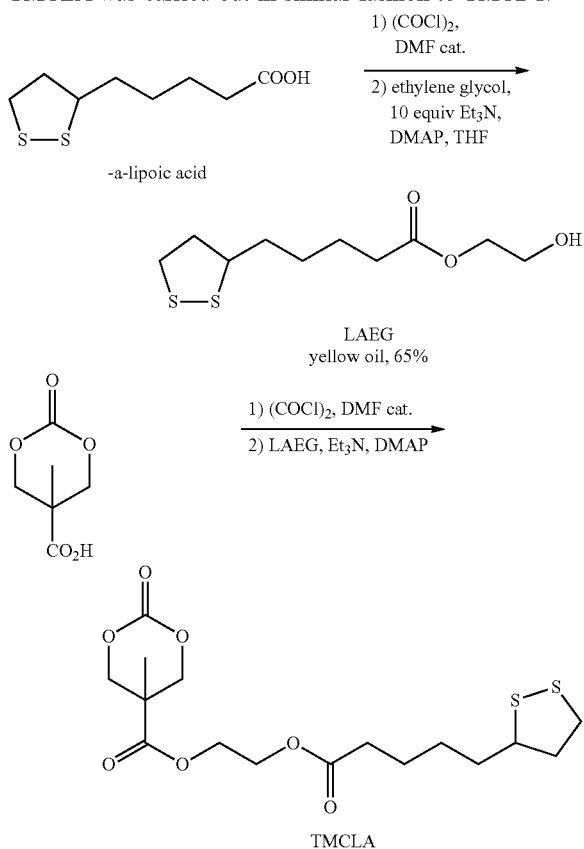

(±)-α-Lipoic acid (0.5 g, 2.4 mmol) was dissolved in 15 mL THF in a dry flask fitted with a magnetic stir bar. The solution was placed under N₂ and DMF (20 μL) was added. (COCl)₂ (0.23 mL, 2.65 mmol, 1.1 equiv) was added dropwise at ambient temperature and the reaction was aged for 3 hours. Ethylene glycol (1.35 mL, 24.0 mmol, 10 equiv) was dissolved in 10 mL THF in another dry flask with a stir bar. Triethylamine (1.1 mL, 7.88 mmol, 3 equiv) was added to the ethylene glycol solution, followed by DMAP (10 mg, 0.08 mmol, 0.03 equiv) and the mixture was cooled in an ice bath under N₂. The acid chloride solution was then introduced via cannula to the ethylene glycol/Et₃N solution over 30 min. The reaction was brought to ambient temperature and stirred overnight (16 h). The reaction was filtered through fritted funnel packed with celite and the ammonium chloride cake was washed with THF. The filtrate was concentrated via rotary evaporation and the residue was chromatographed on silica gel using a 4:1 mixture of dichloromethane and ethyl acetate to give the product LAEG as a yellow oil. (0.39 g, 65% yield). 1H NMR (CDCl3) δ 4.21 (m, 2H), 3.82 (m, 2H), 3.57 (m, 1H), 3.16 (m, 2H), 2.46 (m, 1H), 2.37 (t, J=7.43 Hz, 2H), 1.91 (m, 1H), 1.68 (m, 4H), 1.47 (m, 2H).

5-Methyl-2-oxo-1,3-dioxane-5-carboxylic acid (1.3 g, 8.1 mmol) was dissolved in 50 mL THF in a dry flask under N₂. DMF (50 μL) was added to the mixture, followed by dropwise addition of (COCl)₂ (0.78 mL, 9.1 mmol, 1.1 equiv). The reaction was aged for 3 hours at room temperature. LEAG (1.7 g, 6.8 mmol, 0.85 equiv) was dissolved in 50 mL THF in another dry flask with a stir bar. Triethylamine (2.85 mL, 20 mmol, 2.5 equiv) was added to the LEAG solution, followed by DMAP (80 mg, 0.65 mmol, 0.08 equiv) and the mixture was cooled in an ice bath under N₂. The acid chloride solution was then introduced via cannula to the LEAG/Et₃N solution over 30 min. The reaction was then brought to ambient temperature and stirred overnight (18 h). The reaction was filtered through fritted funnel packed with celite and the ammonium chloride cake was washed with THF. The filtrate was concentrated via rotary evaporation and the residue was chromatographed on silica gel using a 3:2 mixture of ethyl acetate and hexane to give the product TMCLA as a yellow oil (1.5 g, 58% yield). ¹H NMR (CDCl3) δ 4.69 (d, J=11.9 Hz, 2H), 4.41 (m, 2H), 4.32 (m, 2H), 4.20 (d, J=12.0 Hz), 3.57 (m, 1H), 3.17 (m, 2H), 2.47 (m, 1H), 2.35 (d, J=7.4 Hz, 2H), 1.9 (m, 1H), 1.70 (m, 4H), 1.45 (m, 2H), 1.33 (s, 3H).

Preparation of Triblock Copolymers of TMCLA

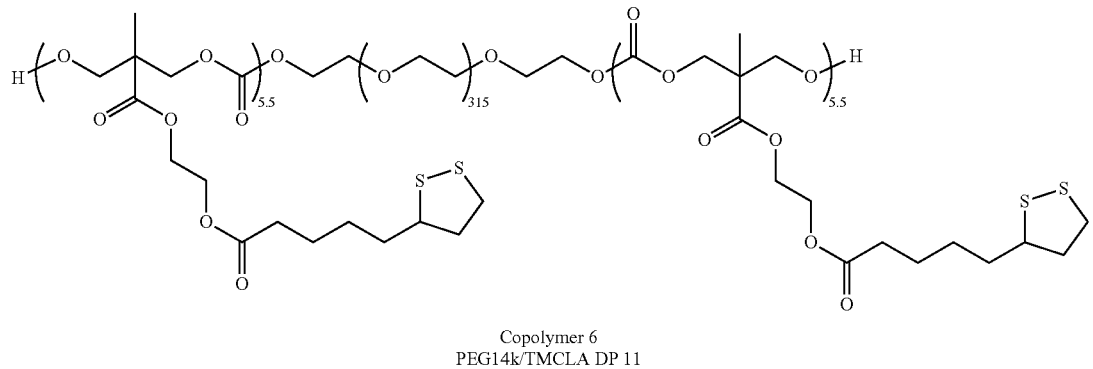

Copolymer 6
PEG14k/TMCLA DP 11

In glove box under $N_2$, PEG 14 k (200 mg, 0.014 mmol), thiourea (4.5 mg, 0.012 mmol) was dissolved in 0.44 mL dichloromethane. TMCLA (0.14 mL of 1.4 M stock solution, 0.196 mmol) was then introduced. DBU (1.2 μL, 0.010 mmol) was added to initiate polymerization and the vial was sealed with a screw cap. After 2 hours, the reaction was quenched by the addition of excess benzoic acid and precipitated three times into diethyl ether (3×300 mL) to give copolymer 5 as a light yellow solid (172 mg, 62% yield). $M_n$=17410 g/mol ($^1$H NMR), PDI=1.18 (GPC). 1H NMR (CDCl3): δ 4.28 (m, 8H), 3.63 (s, 115H), 3.55 (m, 1H), 3.14 (m, 2H), 2.46 (m, 1H), 2.34 (m, 2H), 1.67 (m, 4H), 1.47 (m, 2H), 1.19-1.26 (m, 3H).

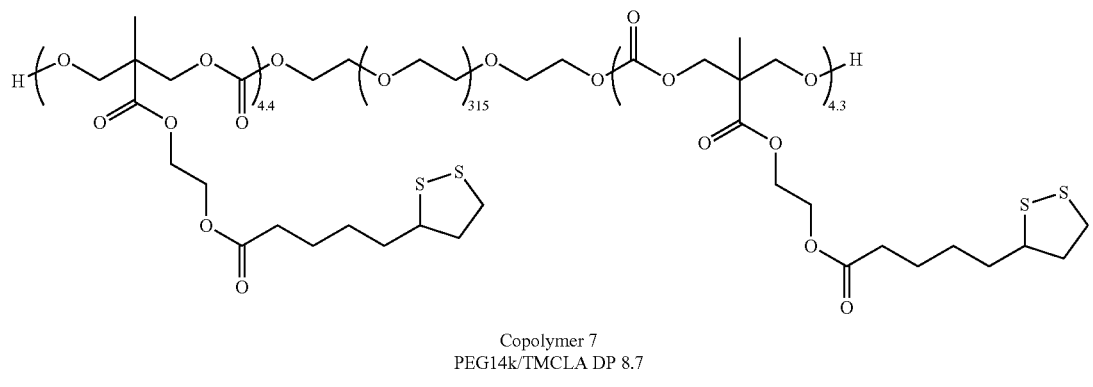

Copolymer 7
PEG14k/TMCLA DP 8.7

In glove box under $N_2$, PEG 14 k (200 mg, 0.014 mmol), thiourea (4.5 mg, 0.012 mmol) was dissolved in 0.45 mL dichloromethane. TMCLA (0.11 mL of 1.4 M stock solution, 0.155 mmol) was then introduced. DBU (1.3 μL, 0.009 mmol) was added to initiate polymerization and the vial was sealed with a screw cap. After 2 hours, the reaction was quenched by the addition of excess benzoic acid and precipitated three times into diethyl ether (3×300 mL) to give copolymer 6 as a light yellow solid (140 mg, 54% yield). $M_n$=18312 g/mol ($^1$H NMR), PDI=1.16 (GPC). 1H NMR (CDCl3): δ 4.28 (m, 8H), 3.63 (s, 150H), 3.55 (m, 1H), 3.14 (m, 2H), 2.46 (m, 1H), 2.34 (m, 2H), 1.91 (m, 1H), 1.67 (m, 4H), 1.47 (m, 2H), 1.19-1.26 (m, 3H).

Thus, by adjusting the monomer/initiator ratios, one may vary the degrees of polymerization of the triblock copolymers. In this pair, copolymer 6 has a degree of polymerization of 11, and copolymer 7 has a degree of polymerization 8.7.

Preparation of a Triblock Copolymer of TMCLA/TMCDT

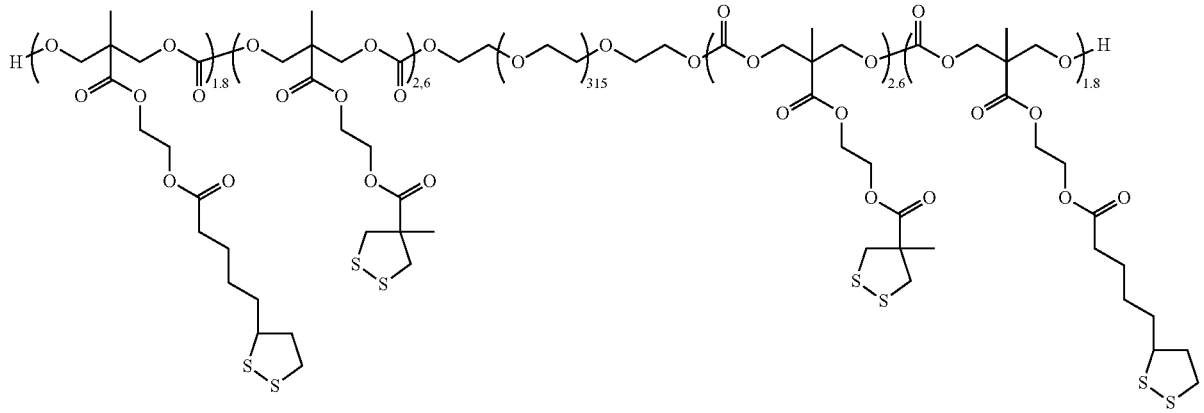

Copylymer 8
PEG14k/TMCDT+TMCLA DP 8.8

In glove box under $N_2$, PEG 14 k (117 mg, 0.0084 mmol), TMCDT (20.8 mg, 0.0594 mmol). thiourea (2.1 mg, 0.0057 mmol) was dissolved in 0.45 mL dichloromethane. TMCLA (0.03 mL of 1.4 M stock solution, 0.042 mmol) was then introduced. DBU (0.65 μL, 0.0044 mmol) was added to initiate polymerization and the vial was sealed with a screw cap. After 1.5 hours, the reaction was quenched by the addition of excess benzoic acid and precipitated three times into diethyl ether (3×300 mL) to give copolymer 7 as a light yellow solid (97 mg, 63% yield). $M_n$=17235 g/mol (1H NMR), PDI=1.17 (GPC). $^1$H NMR (CDCl3): δ 4.33 (m, 8H), 3.63 (s, 123H), 3.55 (m, 0.4H), 3.14 (m, 0.8H), 2.93 (d, J=11.6 Hz, 1.2H) 2.46 (m, 0.4H), 2.34 (m, 0.8H), 1.91 (m, 0.4H), 1.67 (m, 4H), 1.47 (m, 1.6H), 1.41-1.53 (m, 2.57H), 1.19-1.26 (m, 3H).

Copolymerizing TMCDT and TMCLA monomers under the same organocatalytic condition produces a triblock copolymer with a similar architecture to copolymers 6 and 7, and exhibiting a degree of polymerization of 8.8, but having a mixture of pendent lipoyl and methyl asparagusic functionalities. The relative content of the two dithiolane groups can be easily controlled by varying the comonomer feed ratios.

Preparation of Hydrogels

Gels of triblock copolymer 3 were generated by adding 3,6-dioxa-1,8-octanedithiol (ODT, 0.5 equiv. relative to TMCDT) to an aqueous dispersion of the copolymers with mild heating (heat gun). Gelation was rapid, occurring immediately upon cooling to room temperature. A minimum copolymer concentration of approx. 10 wt % was required for stable gel formation. Copolymer 3 was selected for further studies due to its good water solubility compared to 1 and the relative ease of preparing and manipulating 10 wt % solutions compared to those of 4 and 5.

Hydrogels prepared from 10 wt % solutions of copolymer 3 in water by the addition of 0.5 equivalents of 3,6-dioxa-1,8-octanedithiol (ODT) could be readily removed from vials, and were deformable and could easily be shaped and cut with a spatula. A vial inversion experiment shows that the hydrogel derived from 3/ODT flows over long time periods (1.5 hours). In contrast, an analogous gel treated with excess iodoacetamide or maleimide, reagents known to react rapidly with free thiols, was more stable and did not flow over the same time period. Without being limited to theory, this behavior may suggest that the ability of the un-capped hydrogels to flow is due to the reversible exchange of free thiols and reformation of dithiolane rings:

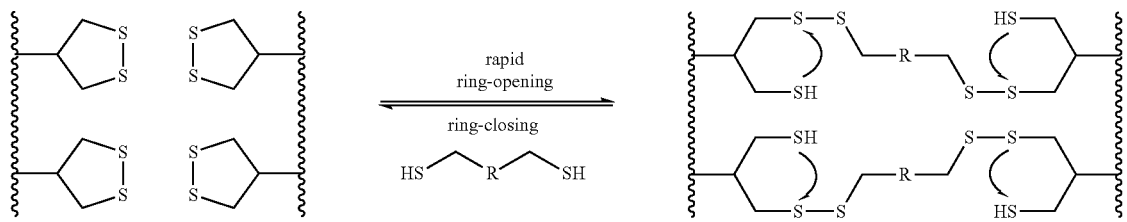

Small Amplitude Oscillatory Shear (SAOS) Rheometry

Small amplitude oscillatory shear (SAOS) rheometry was carried out; initial strain sweeps at a constant oscillatory frequency of 1 Hz showed the hydrogel derived from 3/ODT to be in the linear viscoelastic region from 0.1% strain up to 90% strain with a storage modulus (G') of 2180 Pa and a loss modulus (G") of 860 Pa.

The frequency-dependent moduli G' and G" (25° C.) for the hydrogel derived from 3/ODT reveal that, at high frequencies, the storage modulus G' is higher than the loss modulus G", as expected for a cross-linked network. At lower frequencies, a crossover in the storage and loss modulus occurs consistent with liquid-like behavior at long time scales. This behavior is typical of transient networks and consonant with the visual observations that the gels flow at longer times. At 25° C., the crossover frequency where G'=G"=880 Pa is 0.017 Hz, indicating that at frequencies below 0.025 Hz, disulfide exchange occurs at a rate that allows for dynamic restructuring of the gel.

In contrast, hydrogels 3/ODT treated with an excess of a 1M aqueous solution of maleimide (which reacts rapidly with free thiols) display a higher storage modulus than loss modulus at all accessible frequencies. While not being bound by theory, this change to a predominantly elastic response at all time scales indicates that the presence of free thiols is necessary for dynamic restructuring of the gels, and is consistent with the lack of observed flow in capped hydrogels.

Hydrogels 3/ODT also exhibit thermoreversible behavior. Hydrogels 3/ODT generated at room temperature were observed to flow upon heating to 70-80° C. but reverted to a gel upon cooling to room temperature. As dithiolanes absorb in the UV, this process could also be followed by UV-visible spectroscopy. The triblock polymer 3 containing intact dithiolane rings exhibits a temperature-independent absorbance from ~330-410 nm. In contrast, the hydrogel 3/ODT exhibits an increase in absorbance at ~370 nm with increasing temperature. This behavior is fully reversible over several thermal temperature cycles and is indicative of an increase in the number of dithiolanes with increasing temperature. As the intramolecular cyclization of the mercapto disulfides is expected to be both faster and more favorable at higher temperatures, this process would result in an increase in the rate of crosslink exchange and a decrease in the degree of crosslinking, consistent with the flow behavior observed at higher temperatures.

The hydrogels 3/ODT appear moderately stable under ambient aerobic conditions, at least up to 72 h. Hydrogel samples were kept under ambient air in sealed containers (to minimize evaporation of water) without any special precautions for the exclusion of oxygen. After 48 hours, a reversible temperature-dependent UV/vis absorbance was observed, consistent with the reversible closing and opening of the dithiolane moiety through a free thiol. Additionally, after 72 hours application of a SAOS frequency sweep revealed that hydrogel 3/ODT exhibits rheological behavior similar to those of freshly prepared samples with a comparable crossover frequency of the storage and loss modulus. These data suggest that if any oxidative disulfide formation occurs, it does not appreciably alter the hydrogel properties over these time periods.

Hydrogels based on triblock copolymers were prepared by introducing 3,6-dioxa-1,8-octanedithiol (ODT) (0.6 µL, 0.5 equiv. relative to dithiolane groups) to an aqueous dispersion of the copolymers (13.6 mg in 122 µL water, 10 wt %) with mild heating and vortex. Gelation was rapid, occurring immediately upon cooling to room temperature. The TMCLA hydrogel derived from copolymer 7 exhibits different behavior from the TMCDT based hydrogel derived from copolymer 3. The differences were manifested by oscillatory shear rheometry measurements. The strain sweep suggested that the TMCLA gel from copolymer 7 is more rigid than the TMCDT gel from copolymer 3 with a less liquid-like component. It also does not withstand as much strain as the TMCDT gel before it structurally collapses to become a liquid. A dynamic step-strain test on TMCLA gel shows that it does not recover its mechanical strength after severe strain deformation, indicating a lower self-healing ability of TMCLA gel. TMCLA gel behaves like an elastic material over a large frequency window while TMCDT gel flows and behaves like a liquid at low frequency. There is also a significant difference in the stress relaxation behavior between the two gels: TMCDT gel adapts to the external force and quickly dissipates the energy while TMCLA gel is more resilient against stress and relaxes at a much slower rate. Both gels show a shear-thickening to shear-thinning transition with shear rate but the TMCLA gel shows a higher resistance to flow at low shear rates. The two gels also respond differently to temperature change. While the TMCDT gel exhibits a reversible gel-sol transition at 40° C., TMCLA shows a steady increase in G" and almost constant G' over temperature and no sol-gel transition.

TMCLA gels appear more stable than TMCDT gels upon dilution. While TMCDT gel dissolved completely in PBS buffer in less an hour, the TMCLA gel under the same condition did not dissolve up to 2 days. The solution stability of TMCLA gel makes it useful for applications such as drug delivery or cell culture where a slow degradation profile of the carrier (matrix) is desired.

While not wishing to be held to the theory, the differences in the properties of the gels may be rationalized as a reflection of a different equilibrium of ring-opening/closure between TMCDT and TMCLA. The thermodynamics of thiol-disulfide exchange is known to be sensitive to the substituents on the dithiolane rings. It is possible that the ring-opening of lipoyl groups in TMCLA is less reversible than the ring-opening of methyl asparagusic group in TMCDT, resulting in a more permanent and stable crosslinking of the TMCLA network. In any event, using the same polymer platform and crosslinking chemistry but different dithiolane functionalities, one can prepare hydrogels with properties attuned specifically to various purposes.

Copolymerization of different dithiolane monomers is an alternative strategy to tune the properties of the hydrogels. The hydrogel derived from triblock copolymer 8 showed similar dynamic properties (self-healing and viscoelasticity) to those of pure TMCDT gels but stability against dilution or stress similar to TMCLA gels. These properties may be quantified by oscillatory shear rheometry. The gel based on copolymer 8 has an intermediate G' and G" and stress relaxation rate compared to the TMCDT and TMCLA gels. It exhibited self-healing and viscoelastic behavior similar to TMCDT gel, but is more stable upon dilution than the TMCDT gel. The gel based on copolymer 8 did not fully dissolve in PBS buffer up to 18 hours.

The present invention provides novel compounds and compositions, including a thermoreversible hydrogel that exhibits flow behavior due to the dynamic and reversible ring-opening of 1,2-dithiolanes. Utilizing the dynamic ring-opening/ring-closing of the 1,2-dithiolane structure represents an entry to covalently adaptable networks. The material's behavior can be modulated through the introduction of suitable reagents which undergo rapid and mild reaction with sulfhydryl moieties. Applications for the hydrogel include those requiring shaping and molding of gels at the point of introduction or where network rearrangement over time is required. There is also a potential for use at mucosal surfaces, which contain a high number of free cysteines, where immobilization of the hydrogel could occur through disulfide formation at the mucosa/gel interface.

Amphiphilic ABA triblock copolymers with hydrophobic A blocks and hydrophilic B blocks are known to self-assemble in water to form transient micellar structures at low concentration (above critical micelle concentration). Based on this self-assembly property, a class of polymeric micelles were prepared from the foregoing dithiolane functionalized triblock copolymers using the solvent exchange method. One may theorize that the hydrophobic dithiolane groups can aggregate in the micellar core while the hydrophobic PEG can either loop or extend to form the corona. In the experiments, the size of the micelles ranged from 30 nm to over 200 nm depending on polymer composition, choice of organic solvent, and the organic to aqueous phase ratio. (Table 2)

TABLE 2

Polymer nanoparticles prepared from TMCDT copolymers

| Triblock copolymer | Condition | Z-average (d · nm) | PDI |
|---|---|---|---|
| PEG14k, DP10 | DMSO/H$_2$O 1:4 | 32 | 0.144 |
| PEG14k, DP14 | DMSO/H$_2$O 1:4 | 221 | 0.132 |
| PEG8k, DP10 | DMSO/H$_2$O 1:6 | 215 | 0.102 |
| PEG8k, DP10 | DMSO/H$_2$O 1:4 | 170 | 0.105 |
| PEG8k, DP10 | DMSO/H$_2$O 1:2 | 147 | 0.135 |
| PEG8k, DP10 | DMSO/H$_2$O 1:1 | 64 | 0.251 |
| PEG8k, DP10* | DMSO/H$_2$O 1:2 | 67 | 0.269 |
| PEG8k, DP10 | MeOH/H$_2$O 1:4 | 35 | 0.138 |

*For this example, the particles were formed by reverse addition of water to DMSO.

These polymer nanoparticles are stable in water for over a month without changes in size and polydispersity, indicating the absence of aggregation and negligible degradation of polycarbonate inside the micelles over a long time period. Interestingly, the micelles maintain their sizes even in the presence of high salt concentration (eg. 2 mol/L NaCl), a condition where polymeric micelles tend to aggregate. The nearly neutral surface of the particles (zeta potential <<−10 my) reduces non-specific binding in biological environments.

The dithiolane groups of these materials allow crosslinking the micellar core through the thiol-initiated ring-opening cascade of dithiolanes. The —SH generated from the ring-opening can be further capped with maleimide to prevent the reversible ring closure. The crosslinking increases the stability of the micelles against dilution. Non-crosslinked micelles or the micelles treated with only free thiols readily dissociate in acetone, which is a good solvent for both PEG and polycarbonate blocks. In contrast, micelles that are crosslinked by a thiol crosslinker and capped with maleimide survive in acetone and show a moderate size increase due to swelling of micelle cores.

Examples of potential applications of dithiolane-containing polymer nanoparticles (1) Encapsulation of Gold Nanoparticles Gold nanoparticles (AuNPs) have been widely used in biomedical applications such as imaging contrast agents, therapeutic agents, biological sensors due to their unique properties such as size and shape dependent optoelectronic properties, large surface area, good biocompatibility. To prevent AuNPs from aggregation, a protecting layer of capping ligands is required. The dithiolane-functionalized triblock copolymers described herein may be employed as a protective polymer coating for AuNPs. AuNPs were prepared by a simple reaction between chloroauric acid and NaBH$_4$ according to a literature procedure [Deraedt et al., Chem. Commun 2014, 50, 14194]. The resulting AuNPs have a surface plasmon band at 520 nm and hydrodynamic diameters around 7 nm with low dispersity. Upon the addition of the thiol-containing triblock copolymer generated from the reduction of dithiolane polymer 3 by tris(2-carboxyethyl)phosphine, the surface plasmon band shifted to 535 nm along with a size increase to 32 nm. This indicated a successful encapsulation of AuNPs by the reduced dithiolane polymers. Moreover, the polymer coated AuNPs solution was stable over weeks while the AuNPs lacking protecting ligands aggregated in a few days as evidenced by an increasing absorption at near IR region (>600 nm) and a size increase by DLS, thus demonstrating that the dithiolane-functionalized triblock copolymers can solubilize and protect AuNPs from aggregation.

Administration of hydrophobic drugs is a major challenge in pharmaceutical industry. Hydrophobic drugs are drugs whose water-octanol partition coefficient, expressed as log P$_A$, exhibit a log P$_A$ greater than zero. The design of suitable carriers for hydrophobic drugs can effectively enhance their solubility and prolong the circulation time. Polymeric micelles have various advantages including great cargo capacity, non-toxicity, tailorability and controlled drug release. The hydrophobic core of the dithiolane copolymer-based micelles described herein can incorporate hydrophobic drugs or protein through both hydrophobic interactions and covalent bonds and the crosslinking provides enhanced stability and controlled degradation and release.

Curcumin, with a log P$_A$ of 3.2, serves as a model drug to investigate the potential of the instant polymer micelles as a drug delivery vehicle. Curcumin was loaded to the polymer through nanoprecipitation, and the amount of the drug incorporated into the micelles was determined by UV-vis spectroscopy. A relatively hydrophobic triblock copolymer (PEG4.6 k/TMCDT DP10) copolymer 1, provided a drug loading content of 10.5% and high efficiency (81.5%). Less hydrophobic triblock copolymers appear to provide lower loading ratios and lower efficiencies. Drug loading content $$(\text{wt. }\%) = \frac{\text{weight of loaded drug}}{\text{total weight of loaded drug and polymer}} \times 100\%;$$

$$\text{drug loading efficiency}(\%) = \frac{\text{weight of loaded drug}}{\text{weight of drug in feed}} \times 100\%.$$

The effective concentration of curcumin dispersed in the copolymer 1 micelle solution (187 µg/mL) is more than 300 times higher than its solubility in pure water (0.6 µg/mL). In addition to solubilizing curcumin, the hydrophobic micellar cores also effectively protect curcumin from hydrolysis.

To prepare micelles, 10 mg triblock copolymer was dissolved in 1.0 mL DMSO. The solution was added dropwise to 4 mL deionized water stirring at 1200 rpm. The resulting solution was stirred at room temperature for half an hour and then dialyzed against deionized water to remove DMSO (MW cutoff=3500 Da). The size of the resulting polymeric micelles was determined using dynamic light scattering.

Crosslinking and end-capping of micellar cores was accomplished as follows: A solution of triblock copolymer based micelles in water (above critical micelle concentration) was purged with N$_2$ for 10 min. Catalytic amount of 3,6-dioxa-1,8-octanedithiol (0.1 equiv. relative to dithiolane groups) was introduced to the solution. The solution was vortexed and then kept in the dark for 10 minutes. Maleimide (2 equiv relative to 3,6-dioxa-1,8-octanedithiol) was added to the solution. The solution was vortexed until all maleimide dissolved.

To produce triblock copolymer 9 with pendant thiol groups, the copolymer 3 (PEG14 k/TMCDT DP10, 100 mg) was dissolved in 5 mL water. The solution was purged with N$_2$ for 10 min. A solution of tris(2-carboxyethyl)phosphine hydrochloride (25 mg in 2 mL water, 0.087 mmol, 1.5 equiv to TMCDT) was added to the copolymer solution. The solution was stirred at room temperature under N$_2$ for 30 min. Then the solution was extracted three times with DCM (3×3 mL). The organic phase was dried over MgSO4, filtered, and concentrated to a colorless oil (72 mg, yield ~72%). 1H NMR (CDCl3): δ 4.35 (m, 8H), 3.64 (s, 128H), 2.82 (s, 4H), 1.21-1.30 (m, 6H).

Gold nanoparticles were obtained as follows: HAuCl4.xH2O (50% Au basis, 6.7 mg) was dissolved in 10 mL of deionized water as a stock solution. 1 mL of this stock solution was diluted in 9 mL deionized water to obtain a $[Au]=1.74\times10^{-1}$ mM. After stirring for 5 min, 1.0 mL of a NaBH$_4$ stock solution (1.4 mg NaBH$_4$ in 11 mL, 2 equiv to Au) was added quickly to the solution under vigorous stirring. The solution turned from yellow to pink immediately. After stirring for 10 min, a solution of copolymer 9 (15 mg in 2 mL deionized water) was added to the gold nanoparticle solution. A slight color change from pink to red was observed. The solution was stirred overnight and dialyzed against water (MW cutoff=3500) to get a solution of polymer coated AuNPs.

Loading of curcumin to polymeric micelles. Triblock Copolymer 1 (PEG4.6 k/TMCDT DP10, 10.4 mg) and curcumin (1.52 mg) were dissolved in 1.0 mL DMSO and mixed via vortex. The solution was added dropwise to 3 mL deionized water under stirring at room temperature. The solution was stirred for another 30 min and then dialyzed against deionized water for 24 h (MW cutoff=3500). The solution inside dialysis tubing was collected. The amount of curcumin loaded in the micelles was determined using UV-vis spectroscopy (peak absorption at 430 nm): a small portion of micelle solution was diluted 200 times in ethanol and subjected to UV-vis measurement. The concentration of curcumin was determined using a calibration curve of curcumin in ethanol.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method that "comprises", "has", "includes" or "contains" one or more steps or elements possesses those one or more steps or elements, but is not limited to possessing only those one or more steps or elements.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A hydrogel comprising water and a polymer, said polymer comprising a structural unit of the formula (IV):

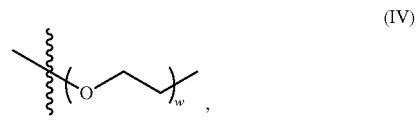

wherein
w is 1-1000;
and a structural unit of the formula (II):

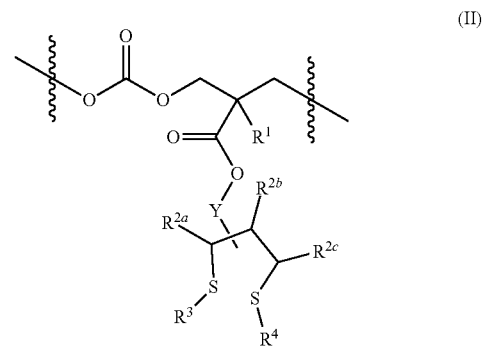

wherein
Y is a linker selected from aliphatic $C_1$-$C_8$ hydrocarbyl in which one or two carbon atoms may optionally be replaced by one or more of —O— and —C(=O)—, and wherein Y is attached to the carbon attached to $R^{2a}$, to the carbon attached to $R^{2b}$, or to the carbon attached to $R^{2c}$;
$R^1$ is selected from hydrogen and $C_1$-$C_3$ alkyl;
$R^{2a}$, $R^{2b}$, and $R^{2c}$, are individually selected from hydrogen and $C_1$-$C_3$ alkyl;
$R^3$ and $R^4$ are hydrogen, or $R^3$ and $R^4$, taken together, form a direct bond between the sulfur atoms to which they are attached, thereby forming a dithiolane ring; or one of $R^3$ and $R^4$ is selected from hydrogen, pyrrolidine-2,5-dione, and propionamide, and the other is a residue of formula (IIIA):

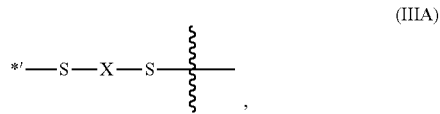

wherein
*' represents the point of attachment to a sulfur of (II);
X is chosen from $C_1$-$C_{10}$ hydrocarbyl, $C_1$-$C_{10}$ hydrocarbyl substituted with —OH, —(CH$_2$)$_q$—O—(CH$_2$)$_r$— and —(CH$_2$)$_q$[—O—(CH$_2$)$_r$]$_t$—;
q is 2, or 3;
r is 2, or 3; and
t is an integer from 2 to 1000.

2. A hydrogel according to claim 1 wherein Y is aliphatic $C_1$-$C_8$ hydrocarbyl in which two adjacent carbon atoms are replaced by —C(=O)O—.

3. A hydrogel according to claim 2, wherein Y is —$(CH_2)_n$—$(O)_m$—$(C=O)_p$—,
wherein
n is 1, 2, 3, or 4;
m is 0 or 1; and
p is 0 or 1.

4. A hydrogel according to claim 3, wherein Y is $(CH_2)_n$—O—C(=O)—.

5. A hydrogel according to claim 4, wherein n is 2.

6. A hydrogel according to claim 1, wherein $R^1$ and $R^2$ are methyl.

7. A hydrogel according to claim 2, wherein Y is —$(CH_2)_u$—O—C(=O)—$(CH_2)_v$—
wherein
u is 2, 3, or 4; and
v is an integer from 1 to 6.

8. A hydrogel comprising water and a polymer, said polymer comprising a structural unit of the formula:

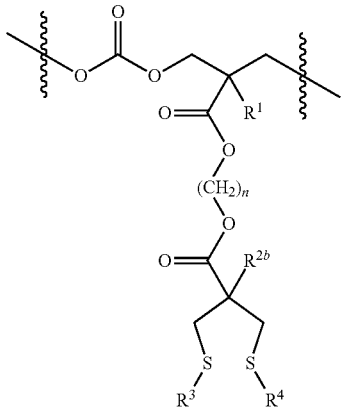

and a unit of formula

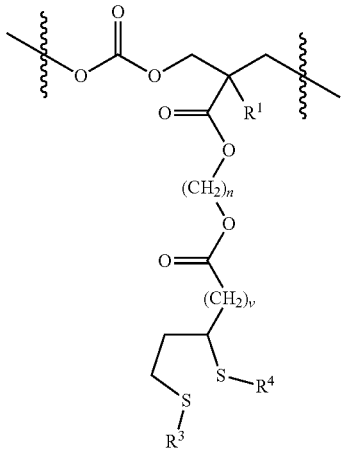

and a unit of the formula (IV):

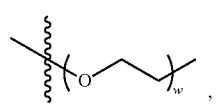

wherein
$R^1$ is selected from hydrogen and $C_1$-$C_3$ alkyl;
$R^{2a}$, $R^{2b}$, and $R^{2c}$, are individually selected from hydrogen and $C_1$-$C_3$ alkyl;
$R^3$ and $R^4$ are hydrogen, or $R^3$ and $R^4$, taken together, form a direct bond between the sulfur atoms to which they are attached, thereby forming a dithiolane ring; or one of $R^3$ and $R^4$ is selected from hydrogen, pyrrolidine-2,5-dione, and propionamide, and the other is a residue of formula (IIIA):

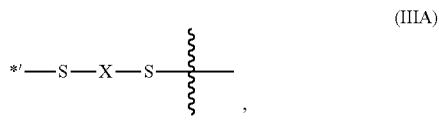

wherein
*' represents the point of attachment to a sulfur of (II);
X is chosen from $C_1$-$C_{10}$ hydrocarbyl, $C_1$-$C_{10}$ hydrocarbyl substituted with —OH, —$(CH_2)_q$—O—$(CH_2)_r$— and —$(CH_2)_q[$—O—$(CH_2)_r]_t$—;
n is 1, 2, 3, or 4;
q is 2, or 3;
r is 2, or 3; and
t is an integer from 2 to 1000;
u is 2, 3, or 4;
v is an integer from 1 to 6, and
w is 1-1000.

9. An encapsulated metal nanoparticle comprising a metal and a polymer comprising a structural unit of the formula (II):

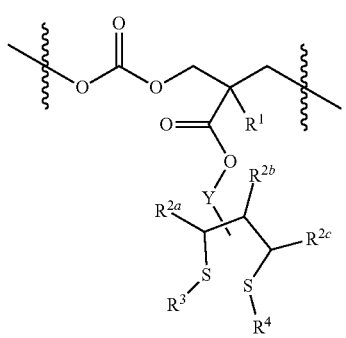

wherein
Y is a linker selected from aliphatic $C_1$-$C_8$ hydrocarbyl in which one or two carbon atoms may optionally be replaced by one or more of —O— and —C(=O)—, and wherein Y is attached to the carbon attached to $R^{2a}$, to the carbon attached to $R^{2b}$, or to the carbon attached to $R^{2c}$;
$R^1$ is selected from hydrogen and $C_1$-$C_3$ alkyl;
$R^{2a}$, $R^{2b}$, and $R^{2c}$, are individually selected from hydrogen and $C_1$-$C_3$ alkyl;
$R^3$ and $R^4$ are hydrogen, or $R^3$ and $R^4$, taken together, form a direct bond between the sulfur atoms to which they are attached, thereby forming a dithiolane ring; or one of $R^3$ and $R^4$ is selected from hydrogen, pyrrolidine-2,5-dione, and propionamide, and the other is a residue of formula (IIIA):

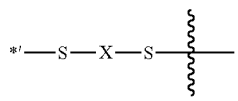
(IIIA)

wherein
*' represents the point of attachment to a sulfur of (II);
X is chosen from $C_1$-$C_{10}$ hydrocarbyl, $C_1$-$C_{10}$ hydrocarbyl substituted with —OH, —$(CH_2)_q$—O—$(CH_2)_r$— and —$(CH_2)_q[$—O—$(CH_2)_r]_t$—;
q is 2, or 3;
r is 2, or 3; and
t is an integer from 2 to 1000 according to claim 1.

10. An encapsulated metal nanoparticle according to claim 9 wherein said metal is gold.

11. A drug-containing micelle comprising a drug and a polymer, said polymer comprising a structural unit of the formula (II):

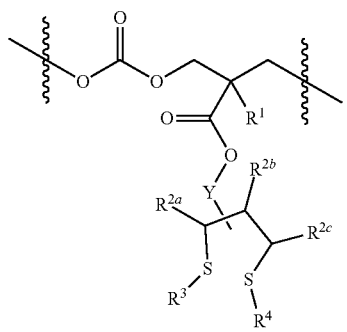
(II)

wherein
Y is a linker selected from aliphatic $C_1$-$C_8$ hydrocarbyl in which one or two carbon atoms may optionally be replaced by one or more of —O— and —C(=O)—, and wherein Y is attached to the carbon attached to $R^{2a}$, to the carbon attached to $R^{2b}$, or to the carbon attached to $R^{2c}$;
$R^1$ is selected from hydrogen and $C_1$-$C_3$ alkyl;
$R^{2a}$, $R^{2b}$, and $R^{2c}$, are individually selected from hydrogen and $C_1$-$C_3$ alkyl;
$R^3$ and $R^4$ are hydrogen, or $R^3$ and $R^4$, taken together, form a direct bond between the sulfur atoms to which they are attached, thereby forming a dithiolane ring; or one of $R^3$ and $R^4$ is selected from hydrogen, pyrrolidine-2,5-dione, and propionamide, and the other is a residue of formula (IIIA):

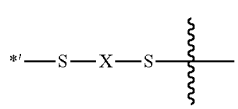
(IIIA)

wherein
*' represents the point of attachment to a sulfur of (II);
X is chosen from $C_1$-$C_{10}$ hydrocarbyl, $C_1$-$C_{10}$ hydrocarbyl substituted with —OH, —$(CH_2)_q$—O—$(CH_2)_r$— and —$(CH_2)_q[$—O—$(CH_2)_r]_t$—;
q is 2, or 3;
r is 2, or 3; and
t is an integer from 2 to 1000 according to claim 1.

12. A drug-containing micelle according to claim 11 wherein said drug is a hydrophobic drug.

13. A process for preparing a polymer having a structural unit of the formula (II):

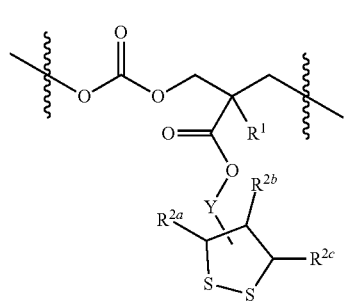
(II)

wherein
Y is a linker selected from aliphatic $C_1$-$C_8$ hydrocarbyl in which one or two carbon atoms may optionally be replaced by one or more of —O— and —C(=O)—, and wherein Y is attached to the carbon attached to $R^{2a}$, to the carbon attached to $R^{2b}$, or to the carbon attached to $R^{2c}$;
$R^1$ is selected from hydrogen and $C_1$-$C_3$ alkyl;
$R^{2a}$, $R^{2b}$, and $R^{2c}$, are individually selected from hydrogen and $C_1$-$C_3$ alkyl;
said process comprising:
performing organocatalytic ring opening polymerization on a compound of formula (I):

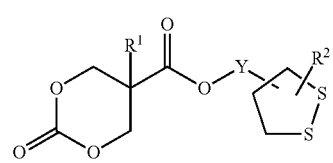
(I)

in the presence of an alcohol, a Lewis base, and a Lewis acid, thereby forming a polymer comprising a structural unit of the formula (II):

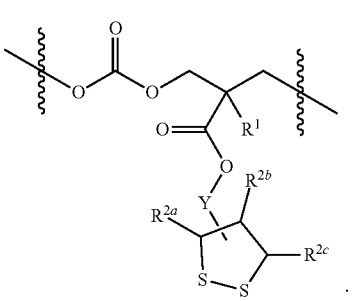
(II)

14. A process according to claim 13, wherein the alcohol is polyethylene glycol.

15. A process according to claim 13, wherein the Lewis base is diazabicyclo [5.4.0] undec-7-ene (DBU).

16. A process according to claim 13, wherein the Lewis acid is a thiourea.

* * * * *